US010692602B1

(12) United States Patent
Nguyen et al.

(10) Patent No.: US 10,692,602 B1
(45) Date of Patent: Jun. 23, 2020

(54) STRUCTURING FREE TEXT MEDICAL REPORTS WITH FORCED TAXONOMIES

(71) Applicant: DEEPRADIOLOGY, INC., Santa Monica, CA (US)

(72) Inventors: Kim Nguyen, Santa Monica, CA (US); Robert Burnham Lufkin, Santa Monica, CA (US); Jameson Tyler Merkow, San Diego, CA (US)

(73) Assignee: DEEPRADIOLOGY, INC., Santa Monica, CA (US)

( * ) Notice: Subject to any disclaimer, the term of this patent is extended or adjusted under 35 U.S.C. 154(b) by 0 days.

(21) Appl. No.: 15/707,918

(22) Filed: Sep. 18, 2017

(51) Int. Cl.
*G06K 9/00* (2006.01)
*G16H 50/20* (2018.01)
*G06T 7/00* (2017.01)
*G16H 15/00* (2018.01)

(52) U.S. Cl.
CPC .......... *G16H 50/20* (2018.01); *G06T 7/0012* (2013.01); *G16H 15/00* (2018.01); *G06T 2207/20084* (2013.01)

(58) Field of Classification Search
CPC ...... G16H 50/20; G16H 15/00; G06T 7/0012; G06T 2207/20084
See application file for complete search history.

(56) References Cited

U.S. PATENT DOCUMENTS

| 5,157,733 | A | 10/1992 | Takeo et al. |
|---|---|---|---|
| 5,790,690 | A | 8/1998 | Doi et al. |
| 5,873,824 | A | 2/1999 | Doi et al. |
| 8,798,345 | B2 | 8/2014 | Sasaki et al. |
| 9,589,374 | B1 | 3/2017 | Gao et al. |
| 10,249,042 | B2 | 4/2019 | Jung et al. |
| 2005/0049497 | A1 | 3/2005 | Krishnan et al. |
| 2005/0283365 | A1 | 12/2005 | Mizutani et al. |
| 2006/0136259 | A1 | 6/2006 | Weiner et al. |
| 2008/0240532 | A1 | 10/2008 | Carneiro et al. |
| 2012/0330876 | A1 | 12/2012 | Bryce |
| 2013/0121548 | A1* | 5/2013 | Kovalan ............... G06T 15/08 382/128 |
| 2013/0339051 | A1* | 12/2013 | Dobrean ............... G16H 15/00 705/3 |
| 2014/0185900 | A1 | 7/2014 | Lee et al. |

(Continued)

OTHER PUBLICATIONS

Alexander J.T. "Practice Policy and Quality Initiatives: Decreasing Variability in Turnaround Time for Radiographic Studies from the Emergency Department" *RadioGraphics* Mar. 2013 vol. 33: 361-371, 10.1148/rg.332125738.

(Continued)

*Primary Examiner* — John W Lee
(74) *Attorney, Agent, or Firm* — Steinfl + Bruno LLP

(57) ABSTRACT

Methods and systems for medical diagnosis by machine learning are disclosed. Imaging data obtained from different medical techniques can be used as a training set for a machine learning method, to allow diagnosis of medical conditions in a faster a more efficient manner. A three-dimensional convolutional neural network can be employed to interpret volumetric data available from multiple scans of a patient. The imaging data can be analyzed according to a forced taxonomy and any discrepancy in the labels of the taxonomy during data analysis by machine learning and human experts can be resolved based on the forced taxonomy.

7 Claims, 6 Drawing Sheets

(56) References Cited

U.S. PATENT DOCUMENTS

| | | | |
|---|---|---|---|
| 2016/0174902 A1 | 6/2016 | Georgescu et al. | |
| 2017/0024887 A1 | 1/2017 | Biegert et al. | |
| 2017/0046616 A1* | 2/2017 | Socher | G06N 3/088 |
| 2017/0091528 A1* | 3/2017 | Savvides | G06K 9/0014 |
| 2017/0098140 A1 | 4/2017 | Wang et al. | |
| 2017/0140240 A1 | 5/2017 | Socher | |
| 2017/0287134 A1 | 10/2017 | Abedini et al. | |
| 2017/0294014 A1 | 10/2017 | Nakano et al. | |
| 2018/0061058 A1* | 3/2018 | Xu | G06N 3/084 |
| 2018/0129911 A1 | 5/2018 | Madabhushi et al. | |
| 2018/0174051 A1 | 6/2018 | Knittel | |
| 2018/0225820 A1 | 8/2018 | Liang et al. | |
| 2018/0232603 A1 | 8/2018 | Shim et al. | |
| 2018/0232883 A1 | 8/2018 | Sethi et al. | |
| 2018/0247416 A1 | 8/2018 | Ruda et al. | |
| 2019/0073569 A1 | 3/2019 | Ben-Ari et al. | |
| 2019/0159744 A1 | 5/2019 | Mensah et al. | |
| 2019/0164278 A1 | 5/2019 | Abramoff et al. | |
| 2019/0164642 A1 | 5/2019 | Hartung et al. | |

OTHER PUBLICATIONS

Bershad E.M. et al., "Multidisciplinary protocol for rapid head computed tomography turnaround time in acute stroke patients" *J Stroke Cerebrovasc Dis*.Jun. 2015; 24(6):1256-1261.

Brady A. et al., "Discrepancy and Error in Radiology: Concepts, Causes and Consequences" *The Ulster Medical Journal*2012; 82(1):3-9.

Girshick R et al. "Fast R-CNN" *International Conference on Computer Vision*2015.

Girshick R. et al., "Rich feature hierarchies for accurate object detection and semantic segmentation" *Computer Vision and Pattern Recognition*2014.

Gunn A.J. "Toward improved radiology reporting practices in the emergency department: a survey of emergency department physicians" *J Radiol Radiat Ther*2013 1(2):2013.

He K. et al., "Deep Residual Learning for Image Recognition" arXiv.org vol. cs.CV.Dec. 10, 2015.

Hinton G. et al., "Distilling the knowledge in a neural network" *arXiv preprint arXiv*:1503.025322015.

Honari et al., "Recombinator Networks: Learning Coarse-to-Fine Feature Aggregation" arXiv.org vol. cs.CV. Nov. 23, 2015.

Ioffe et al., "Batch normalization: Accelerating deep network training by reducing internal covariate shift." arXiv preprint arXiv:1502.03167, 2015.

Kirillov A. et al., "Joint Training of Generic CNN-CRF Models with Stochastic Optimization" *arXiv*:1511.05067v3 [cs.CV]Sep. 14, 2016.

Krizhevsky A. et al., "Imagenet classification with deep convolutional neural networks" *Advances in Neural Information Processing System*1097-1105,2012.

Lai M. "Deep Learning for Medical Image Segmentation" arXiv.org vol. cs. LG May 8, 2015.

Lee et al., "Deeply-supervised nets" *Aistats*2015.

Lee K. et al., "Recursive Training of 2D-3D Convolutional Networks for Neuronal Boundary Prediction" *Advances in Neural Information Processing Systems*pp. 3559-35672015.

Lenc K. et al., "Understanding image representations by measuring their equivariance and equivalence" arXiv preprint arXiv:1411.5908, 2014.

Mahendran A et al., "Understanding deep image representations by inverting them" arXiv preprint arXiv:1412.0035, 2014.

Merkow et al., "Structural Edge Detection for Cardiovascular Modeling" *Medical Image Computing and Computer-Assisted Intervention—MICCAI 2015. Springer*,2015 735-742.

Merkow J. et al., "Dense Volume-to-Volume Vascular Boundary Detection" *International Conference on Medical Image Computing and Computer-Assisted Intervention*2016.

Non-Final Office Action for U.S. Appl. No. 15/709,223, filed Sep. 19, 2017, on behalf of Deepradiology, Inc. dated Sep. 18, 2018. 8 pgs.

Non-Final Office Action for U.S. Appl. No. 15/709,293, filed Sep. 19, 2017, on behalf of Deepradiology, Inc. dated Nov. 21, 2018. 11 pages.

Non-Final Office Action for U.S. Appl. No. 15/711,541, filed Sep. 21, 2017 on behalf of Deepradiology, Inc. dated Mar. 4, 2019. 16 pages.

Non-Final Office Action for U.S. Appl. No. 15/707,942, filed Sep. 18, 2017 on behalf of Deep Radiology Inc. dated Jun. 26, 2019 13 pages.

Notice of Allowance for U.S. Appl. No. 15/709,223, filed Sep. 19, 2017 on behalf of Deep Radiology Inc dated Jul. 1, 2019 8 pages.

Notice of Allowance for U.S. Appl. No. 15/709,293, filed Sep. 19, 2017 on behalf of Deep Radiology Inc dated Jun. 12, 2019 8 pages.

Pinto A. et al., "Spectrum of diagnostic errors in radiology" *World of Journal of Radiology*2010;2(10):377-383.

Ren S. et al., "Faster R-CNN: Towards real-time object detection with region proposal networks" *Advances in Neural Information Processing Systems*2015.

Restriction Requirement for U.S. Appl. No. 15/398,635, filed Jan. 4, 2017, on behalf of Deepradiology, Inc. dated Dec. 11, 2018. 5 pages.

Restriction Requirement for U.S. Appl. No. 15/712,030, filed Sep. 21, 2017 on behalf of Deepradiology Inc. dated Feb. 28, 2019. 5 pages.

Roth H.R. et al., "DeepOrgan: Multi-level Deep Convolutional Networks for Automated Pancreas Segmentation" arXiv.org2015.

Rumelhart D.E. et al., "Learning representations by back-propagating errors" *Nature*vol. 323, p. 533-536,1986.

Rumelhart et al "Learning internal representations by error propagation, Parallel distributed processing: explorations in the microstructure of cognition" vol. 1 pp. 318-362, *MIT Press Cambridge*, MA, USA,1986.

Saver J.L. "Time to treatment with intravenous tissue plasminogen activator and outcome from acute ischemic stroke" *JAMA*Jun. 2013; 309 (23): 2480-2488.

Shen W. et al., "Multi-scale Convolutional Neural Networks for Lung Nodule Classification" *IPMI*2015.

Sun M. et al., "Multiple Instance Learning Convolutional Neural Networks for Object Recognition" arXiv.orgOct. 2016.

Szegedy C. et al., "Going deeper with convolutions" *Proceedings of the IEEE Conference on Computer Vision and Pattern Recognition*2015.

Tran et al "Deep End2End Voxel2Voxel Prediction" arXiv.org vol. cs.CV. Nov. 20, 2015.

Wang et al., "Training Deeper Convolutional Networks with Deep Supervision" ArXiv 1505.02496 May 11, 2015.

Wong W. et al., "Outsourced teleradiology imaging services: an analysis of discordant interpretation in 124,870 cases" *J Am Coll Radiol*.Jun. 2005; 2(6): 478-484.

Zheng Y. et al., "3D Deep Learning for Efficient and Robust Landmark Detection in Volumetric Data" *SpringerLink*Nov. 2015.

* cited by examiner

STRUCTURING FREE TEXT MEDICAL REPORTS WITH FORCED TAXONOMIES

CROSS REFERENCE TO RELATED APPLICATIONS

The present application may be related to U.S. patent application Ser. No. 15/398,635, filed on Jan. 4, 2017, the disclosure of which is incorporated herein by reference in its entirety.

TECHNICAL FIELD

The present disclosure relates to medical diagnosis. More particularly, it relates to structuring free text medical reports with forced taxonomies.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
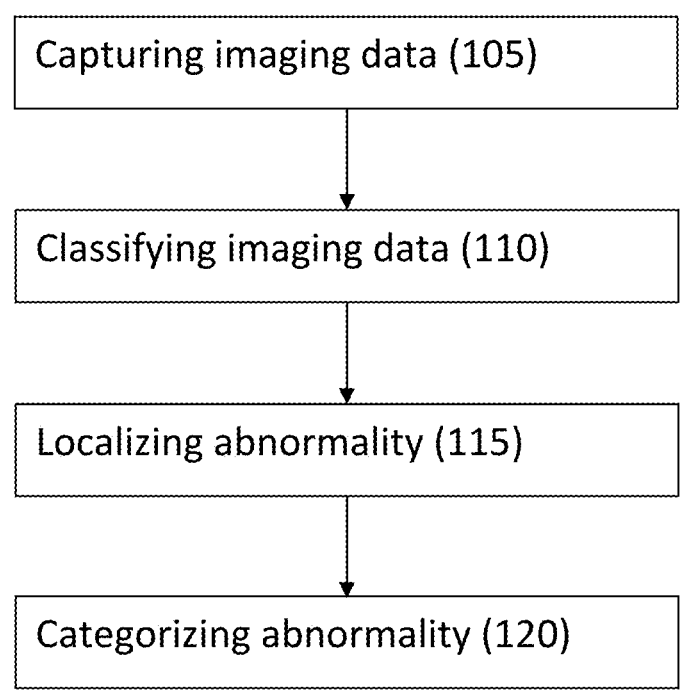
FIG. 1 illustrates an overview of one embodiment of a diagnosing process of the present disclosure.

In a first aspect of the disclosure, a device is described, the device comprising: a processor and memory configured to implement the steps of: receiving imaging data relating to a body part of a human patient; receiving a taxonomy of labels describing a plurality of normal and abnormal conditions for the body part, the taxonomy of labels describing the normal and abnormal conditions in the imaging data; and classifying by machine learning the imaging data into a normal or an abnormal class by selecting or not selecting each label of the taxonomy of labels.

In a second aspect of the disclosure, a method is described, the method comprising receiving, by a computer, imaging data relating to a body part of a human patient; receiving a taxonomy of labels describing a plurality of normal and abnormal conditions for the body part, the taxonomy of labels describing the normal and abnormal conditions in the imaging data; and classifying by machine learning the imaging data into a normal or an abnormal class by selecting or not selecting each label of the taxonomy of labels.

DETAILED DESCRIPTION

The present disclosure describes methods for automated curation of medical reports analyzed with machine learning algorithms. The networks that analyze the medical reports of medical tests based on machine learning are trained on annotated reports. These training cases for deep learning systems are annotated using forced taxonomies.

Technical reports produced to describe findings in imaging studies (such as medical imaging) are typically structured as freeform prose. For example, medical doctors may annotate such imaging studies (e.g. CT scans or x-rays) with a variety of different terminology. While the terms used to describe structures or anomalies in an image can be similar, they are often nevertheless not identical.

The use of freeform prose by medical doctors allows tremendous flexibility in the reporting language but results in great variability in the report content. The variability increases the possibility of miscommunication and limits the usefulness of the information for the training and development of artificial intelligence systems such as deep learning. Therefore, it may be advantageous to automatically process the reports to render the annotation uniform in a way that can be understood by a machine learning network. In this way, the reports can be more effective in training and ultimately render the machine learning network more effective in detecting abnormalities in new reports.

The present disclosure describes methods which process the technical reports and force a given structure onto the report, the structure corresponding to the taxonomy of the deep learning algorithms of the artificial intelligence (AI) systems. This allows the AI/deep learning systems to process the data in an imaging study in real-time as the report is generated.

The methods described in the present disclosure allow several advantages in the automated generation of new medical reports. In situations where the human reader is considered to be an expert with ground truth knowledge, the agreement or disagreement between the human expert and the AI/deep learning system cannot be immediately used for real-time feedback for development and training of the system, unless the ground truth from the expert is immediately available. Generally, the human expert does not analyze a medical imaging study in real-time, due to their limited availability. By contrast, an automated system can analyze an imaging study in real-time.

In situations where the AI/deep learning system is assumed to be the expert with defining knowledge of the domain, the human reader is in training with less overall subject knowledge. For example, a fully trained AI system may possess more knowledge than a medical student. In these cases, the student may train by using the responses by the AI system as the ground truth. In this situation, agreement or disagreement of the human and AI System, as well as the specific findings that the disagreement is regarding in the case of a disagreement, is communicated to the trainee for real-time feedback to improve the performance of the human student.

In yet other situations, the human reader and the AI/deep learning system are both assumed to be operating at a high level of expertise. In this situation, if there is a disagreement between the AI and human on a given real-time case, the human is informed and asked to re-examine the images and reconsider their report. If, after re-examining the study, the human agrees with the AI, then the AI generated report can be issued and accepted as the official report for the image or images. If, after reviewing the images, the human still disagrees with the AI, the study can be sent for immediate review by a second human domain expert.

If the second expert agrees with AI system, then the AI's report can become the official report for those images. In addition, the initial human reader can receive feedback from the AI on the particular part of the human generated report that is in error. If the second expert agrees with the initial human reader, then the images as well as the particular point of disagreement can be used as training data to immediately retrain the AI system in order to minimize the chance of making the same error again.

Therefore, the present disclosure describes how structured reporting can be used in conjunction with deep learning or AI taxonomies, with the specific purpose of training humans and AI systems with real-time feedback of images, as the images are being processed.

In some embodiments, the AI systems described herein can be used with medical imaging, for example radiological studies of CT scans of the head. The taxonomy that is employed was specifically developed for training deep learning/AI systems based on large amounts of patient data, known medical pathophysiology, as well as the specific technical needs for deep learning/AI systems. The taxonomy can be used with real-time CT scans of actual patients that are being interpreted by the radiologist in real-time as part of the overall healthcare diagnosis and therapy of the patient. For example, in some embodiments, the human radiologist is assumed to be the domain expert and any disagreements are used to train the AI system using the specific images and training labels generated by the system based on the disagreement.

As discussed previously herein, in some embodiments the system of the present disclosure may also be used to train human students which then receive feedback from the AI on the particular aspect of their report which disagrees with the domain expert/AI. This feedback is at a very granular level indicating the image and the particular area of the knowledge taxonomy that is in error.

The systems described herein may also be used with both the human and the AI/deep learning system assumed to be domain experts. In this situation any potential disagreements between the AI and the human are reviewed and if needed adjudicated by another expert third-party. In this case, the errors of the AI/deep learning system and the human reader tend to cancel each other out and therefore improve the overall accuracy and performance of the system. In fact, it has been noted that, for a variety of reasons, errors in automated analysis and human analysis generally tend to occur in different way or generally be of different type.

As described above, interpretation of medical imaging studies by expert readers results in a report containing findings that were appreciated in the images. For example, a report may find an abnormality in a specific anatomical region present in an image of the medical scan. Such reports are typically free form text which varies significantly from writer to writer, even for the interpretation of the same set of images.

For supervised learning techniques in deep learning it is advantageous to have consistent 'labels' for each image that reflect the contents of these images. These labels are based on taxonomies that are developed specifically for the deep learning environment based on the imaging study modality and anatomic area.

To be optimally effective in training the networks these labels should conform to a standard taxonomy that is developed for each imaging study type, e.g. scan modality or anatomical area. The present disclosure describes the creation of structured reports that directly follow the optimal taxonomies. As a consequence, the number of options found in a free text document is limited, thereby forcing the report to follow the structure of the taxonomies.

Once the report is produced, if all 'normal' sentences are selected, then the study is automatically labeled 'normal' and each slice in a multislice study will be labeled 'normal'. If one of the 'normal' sentences is replaced with an 'abnormality 1' sentence, then the study will be labeled as containing an abnormality.

The methods described herein may be applied in different fields, not limited to radiology or other areas of medical imaging such as pathology (histology, cytology, electron microscopy), cardiology, dermatology, ophthalmology, and others. The methods may also be applied in fields beyond medical imaging, such as any type of technical reporting that is generated based on the contents of images, for other types of information.

Figure 5:
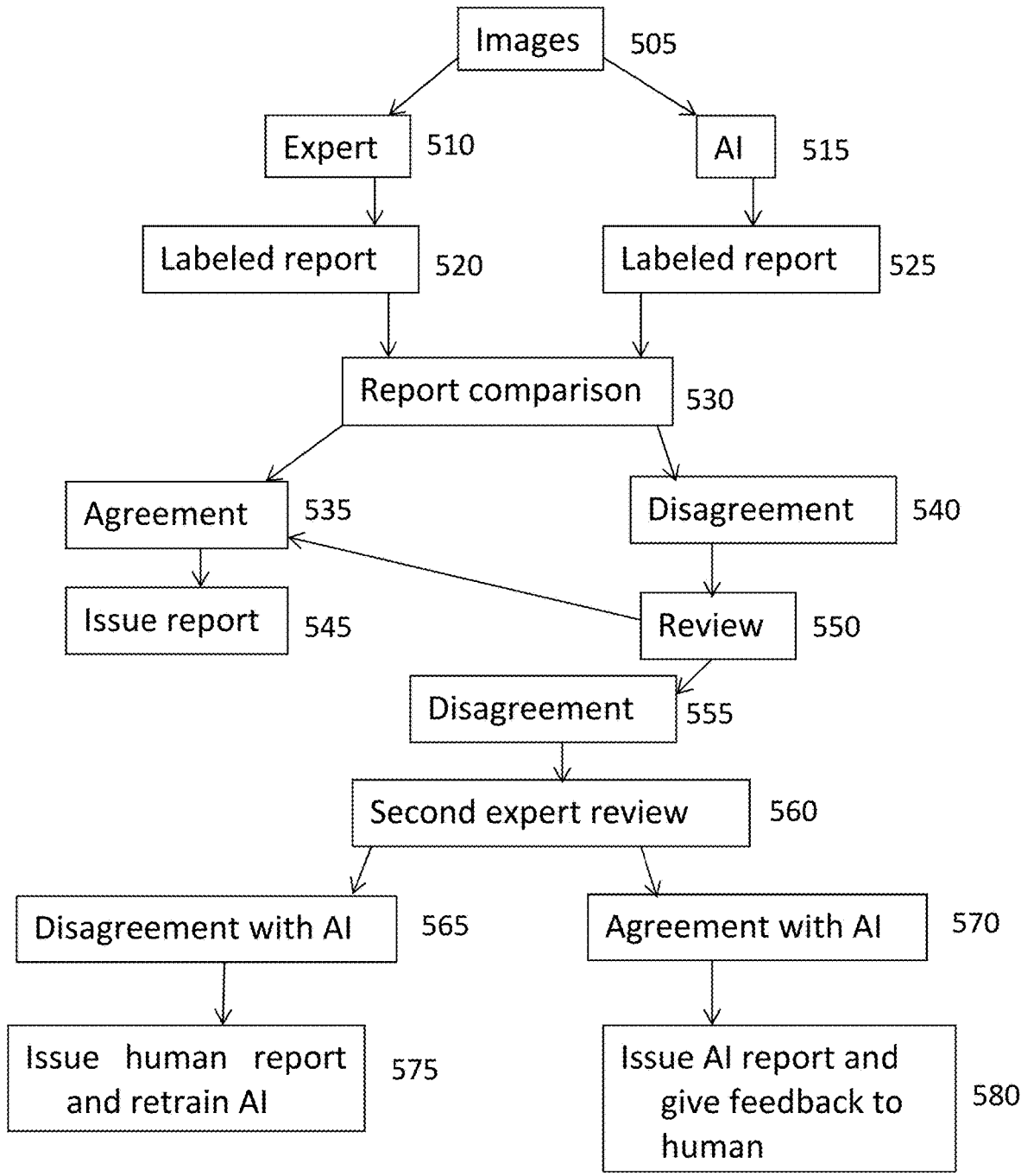
FIG. 5 illustrates an exemplary flowchart for the methods of the present disclosure.

FIG. 5 illustrates an exemplary flowchart for the methods of the present disclosure. The images obtained (505) are reviewed by a human expert (510) and an AI system (515), both generating a labeled report with forced taxonomy. In other words, both the AI and the human expert have a limited amount and type of labels from which to choose when generating the report. For example, a human expert may state that a certain anatomical part is abnormal, but may do so using different terminology which can easily be understood by another human expert. However, forcing the human expert to choose from a specific 'abnormal' label instead of using a freeform label increases the capacity of the AI to read the human-generated labels.

The report labeled by the human (520) may contain labels 1, 2, 3 and 4, with only label 3 ticked off out of the four possible labels. The report labeled by the AI (525) may contain labels 1, 2, 3 and 4, with labels 1 and 3 ticked off out of the four possible labels. The AI can then compare the two reports (530). If the reports are in agreement (535), the report can be issued (545). If the reports are in disagreement, as in the four labels example above (540), a further review step is undertaken (550). For example, the AI may highlight the discrepancy in the labels and request human review of the specific discrepancy. The human review may be requested from the same expert. If the new review by the same human expert finds agreement with the AI, the report can be issued. In this case, the human may recognize their own mistake and determine the AI's interpretation was instead correct.

If the human expert is still in disagreement with the AI (555), a report from a second expert may be requested (560). For example, a second human expert may be sent the specific labeled image which contains a disagreement in the labels. If the second human expert also disagrees with the AI (565), the AI is considered as mistaken. The human report can be issued (575), and the AI is retrained.

If the second human expert is in agreement with the AI (570), the AI report can be issued (580) and feedback provided to the first human expert. In the example with four labels, above, the AI would be retrained to have no label 1 ticked off. Otherwise, if the AI was correct, the first human expert would be sent the image with a comment that the report was missing label 1. In some embodiments, additional human experts may be invited to review the discrepancy, for example reiterating the method above with a third human expert review.

An exemplary forced taxonomy may comprise a list of labels that a human can tick off or not, according to their interpretation of the medical image. For example, for a CT scan of a head without contrast, the report findings may comprise the following labels. If report template may state "The brain parenchyma is normal", so that if no abnormal labels are ticked off in this category, the report automatically includes the sentence describing the category as normal. If the human expert ticks off any of the labels in this category, the sentence containing "normal" is automatically not included. For example, under this category, three exemplary labels could be "Volume loss—cerebral and cerebellar"; "Chronic white matter microvascular ischemia"; and "There is focal encephalomalacia likely related to prior infarct/lacune". The human expert may tick off one or more of the three labels in this category.

In a second category, the "normal" sentence label may be "The paranasal sinuses are clear", followed with the possible abnormal label "There is mild to moderate paranasal sinus disease". A third category may comprise the labels "The mastoids are clear" and "There is otomastoid opacification". A fourth category may comprise the labels "The orbits are unremarkable" and "Post operative orbit changes are present". A fifth category may comprise the labels "The scalp, calvarium, and skill base are unremarkable" and "Scalp swelling is present". Other labels may be included, or a different wording for the exemplary label above may be used. The forced taxonomy, however, relies on ensuring that the labels are uniformly used, so that the AI can easily read the labels generated by a human expert. The same forced taxonomy can be implemented in reports generated by different human expert. The same forced taxonomy can also be used by the AI during training and during the analysis of new images.

In some embodiments, therefore, the forced taxonomy comprises a plurality of labels, the labels describing normal and abnormal conditions of an anatomical body part in the captured imaging data. The labels are selected or not selected, thus forming a report prepared by either the AI or the human expert. The imaging data can comprise X-ray slides, computerized tomography, magnetic-resonance, diffusion-tensor (DT), functional MR, gene-expression data, dermatological images, or optical imaging of tissue slices, or other types of medical scans.

Formalization

If $\{x\_i, =1, \ldots, N\}$ are N studies (each comprising a collection of images, and being in turn an array of positive numbers corresponding to the intensity of each pixel in each image), and y is a binary class variable, for instance y=0 for normal (negative) and y=1 for abnormal, then a classifier is a function y=f(x) that for any study x returns a binary value, for instance 0 if the study is negative or 1 if the study is positive. Sometimes the classifier is written in the form sign(f(x)), in which case f is known as the discriminant. For categorization, the class variable is not binary but instead belongs to a finite set y=1, ..., M, of M diseases and their stage or severity. For detection/localization, the function f is defined at each voxel or pixel in each image x, where it returns a class label y.

For the case of binary classification, type-2 error (missed detection or false negative) refers to a classifier returning a value, for instance f(x)=0 (normal) when the true diagnosis is y=1 (abnormal). Type-1 error (false alarms, or false positive) refers to a classifier returning f(x)=1 (abnormal) when the true diagnosis is y=0 (normal). The cost of these two errors is usually different in medical diagnosis, as a type-1 error may cause un-necessary treatment but otherwise no major harm to the patient, whereas a type-2 error may have fatal consequences or result in malpractice suits. The performance of a classifier is measured by the average number of errors multiplied by the cost of each error, for example $c\_1$ for type-1 errors and $c\_2$ for type-2. This can be termed the (average) risk. A good classifier is one that minimizes risk.

The average entailed in the computation of risk is performed with respect to the probability of each type of error, leading to the expected risk. This process requires knowledge of the joint distribution p(x,y), which is usually unknown. However, a training set may be available, consisting of samples $(x_i, y_i)$ or p(x,y) of imaging studies $x_i$ with their "true" diagnosis $y_i$, for instance performed by a trained physician and double-checked by a second physician independently (ground truth). Therefore, it is possible to compute the empirical risk, which is the sample approximation of the expected risk.

In Machine Learning, the classifier f is chosen from a class of functions, usually dependent on a set of parameters w, so f=f(x;w), which are chosen so as to minimize the risk. Ideally, it is desirable to minimize the expected risk, but since that is not known, it is possible to instead minimize the empirical risk, with the value of the risk at the minimum known as training error. Generally, there is no guarantee that a classifier minimizing the training error also minimizes the expected or test error: that is the error averaged over samples that are not included in the computation of the training error (and therefore not used in the determination of the parameters w). Indeed, it is possible for a classifier to make the training error small, and yet yield a high test error, a phenomenon known as overfitting. Much of the effort undergone during the past several decades in the fields of Machine Learning (ML), Pattern Recognition, and Statistical Inference has been to devise methods that, by means of minimizing the empirical risk or a regularized version thereof, are also guaranteed or at least empirically proven to yield good expected risk. Regularization refers to additional criteria, complexity constraints or bounds, or terms in a cost function that penalize certain solutions, see Ref [31]. Regularization is now commonplace in machine learning and covered in textbooks, see Ref [9].

Deep Learning (DL) is a subfield of ML whereby the function f(x;w) is implemented using a neural network (NN) with multiple hidden layers. A NN is a computational model that corresponds to a statistical graphical model whereby each "visible node" represents a measurement and each "hidden node" represents a random variable, with interconnections between nodes representing statistical dependency. Each node is meant to represent a "neuron" or neural computational unit, and performs linear operations (weighted averaging or convolution) of the output of connected neurons, followed by some kind of non-linearity operation, such as a sigmoidal function or rectified linear unit (ReLU) to yield the output. Neurons are typically connected between layers, but not within layers. However, there exist multiple architectures, so this particular choice should be considered as an example and not a limitation. The algorithm to minimize the empirical risk is a computationally efficient rendition of the chain rule (see Ref. [24]) and is known as "back-propagation". In other words, neural networks are a collection of algorithms, where computation is performed by discrete modules, or "neurons" (herein also termed "nodes"), using network parameters (weights) that are determined during a training phase so as to recognize patterns. Recently, deep convolutional networks have enjoyed a surge in popularity due to their performance in detecting, recognizing and categorizing objects in natural images, see Ref. [10]. Deep Learning can be understood as a collection of generic methods for function approximation, and in particular for approximations of an arbitrary discriminant given sufficient computational and training resources. Therefore, DL can be applied and has been applied to a variety of data sources and tasks. However, in the present disclosure the focus is on the use of DL for the analysis of medical images that have characteristics that are well suited, in particular, to deep convolutional networks (CNN, or convolutional neural networks). For finite computational and training resources, straightforward application of a CNN architecture designed for natural images does not take into account and exploit the particular restrictions imposed by medical images.

In deep learning, neural networks comprise multiple layers, with each layer comprising one or more nodes. For example, a neural network may comprise an input layer, a hidden layer, and an output layer. In some embodiments, the input layers may comprise input data, for example from a set of medical images. Subsequent, hidden layers may weigh values from the input layers according to a set of parameters and functions, and detect features in the data. In some embodiments, subsequent layers are able to detect increasingly complex features in the data. For example, if the data comprises human faces, some layers may detect small facial features and subsequent layers may combine the smaller facial features to detect a specific face.

In some embodiments, CNNs are feed-forward neural network. In other words, the layers feed their numerical values forward to subsequent layers, and do not create loops by feeding to previous layers. In other embodiments, other types of neural networks may be used.

In machine learning, a convolutional neural network is a type of feed-forward artificial neural network in which the nodes respond to a specific input field. The input fields of different nodes can partially overlap. The output of an individual node to its input field can be computed mathematically by a convolution operation. A convolution operation is a mathematical operation on two functions which produces a third function. Generally, a convolution can be obtained integrating the pointwise product of the two functions, as a function of the relative translation between the two functions.

Deep Learning for Medical Imaging

The use of deep learning techniques in medical imaging is rather recent. In 2015, Medical Image Computing and Computer Assisted Intervention (MICCAI) conference—one of the premier conferences in medical imaging—featured a workshop on deep learning in medical imaging. For the most part, this consisted of the rote application of computational methods employed in natural images to medical images.

First, natural images are subject to nuisance variability such as scaling (any given object can project on a region of arbitrary size, from less than one pixel to the entire image, depending on where it is in space and the distance to the camera) and occlusion (only an arbitrary subset of an object, of arbitrary size and shape, can be visible depending on other objects occluding it) that are not present in medical images. In medical images, the voxel size or pixel size is typically known in metric units, and there are no occlusions. Instead, what is measured is absorption or density of tissue at each voxel. Furthermore, medical images are captured under controlled settings where, normally, the patient is approximately positioned in a pre-defined manner, so the data is naturally approximately registered and relatively translation-invariance of the classifier is not necessary the way it is in natural images where a given object can appear anywhere in the image. Therefore, the variability due to transformations of the image domain (the volume, or the imaging plane) can be largely attributed to intrinsic, as opposed to nuisance, variability.

Intrinsic variability refers to the inter-subject variability (the same healthy tissue may appear different in different subjects) and even intra-subject variability (the same patient may show differences in longitudinal studies taken at different instants in time, while still remaining within the bounds of the same class, for example the normal class). Similarly, in natural images, significant illumination changes have to be discounted as the same object can appear under direct illumination, cast shadow, multiple illumination sources, and the illuminant is in general unknown. In medical imaging, the probing signal is controlled, and therefore—except for global variability due to different sensor calibration or probing sequence design—the variability due to the transformation of the image range (the intensity or absorption) can be largely attributed to intrinsic variability. This is unlike natural images where the actual intensity of a pixel is largely irrelevant and contrast transformations are discounted by learning or design, through the use of contrast-invariant filters. In particular, in DL methods, such local contrast variability is "trained away" by presenting multiple images taken under different illumination, and is manifested in the contrast-invariant nature of the learned filters in the first layer. As it has been observed multiple times, first-layer filters resemble Gabor filter banks, which implement local regularized derivatives and are invariant or insensitive to contrast changes.

Additionally, medical images are typically samples of a volume, so the computational architecture of networks designed for the analysis of images, for instance convolutional neural networks (CNN), is not well adapted to them. Even though the filters and feature maps in CNNs are "three-dimensional", in the sense that filters and feature maps have two spatial dimensions plus one "channel" dimension, convolutions are performed by translating the filters along a planar domain. i.e., current CNNs perform two-dimensional convolutions of three-dimensional filters. Medical appearance features exist across three spatial dimensions; therefore it can be advantageous to process this data in three dimensions where these features exist. These requirements call for the development and utilization of techniques for three-dimensional convolutional neural networks (3DCNNs), that exploit the availability of volumetric data, and that enables its full use in the diagnosis. This method is unlike all prior known work in the use of deep learning for medical imaging, where individual slices in a volume are classified independently. Some existing works, making reference to 3D convolution components, apply patch-based volumetric classification. For example, Ref [4], which fails to capture the global and context characteristics of the volume that are important for diagnosis. Other works utilize separable filters, see Ref. [28], thus forgoing the full power of CNNs to learn the most discriminative filters, or apply 3D convolution in a restrictive manner as part of an overall structure that is not fully 3D. Actual 3D Convolution-based NN have appeared only recently and only applied to the analysis of video data (see Ref [3]) demonstrated in segmentation, optical flow estimation and video coloring. Video is fundamentally different to medical imaging volume as the three dimensions do not share a metric; the time-dimension is causal (there is an ordering), and the temporal statistics are substantially different from the spatial ones.

Furthermore, significant prior knowledge on the anatomical structures being imaged is available, some of which is represented in the training set, some of which is captured by generic regularizers (compactness and smoothness of the interface between anatomical structures), and some of which is encoded by knowledge of the anatomy. Such knowledge is available to trained professionals, and should not be discarded. These considerations call for the development and utilization of techniques for "deep supervision", whereby knowledge of anatomy and physiology can be exploited during the training phase of a deep network, beyond the simple supervision using binary (or multi-class) networks. No existing application of deep learning to medical imaging makes use of deep supervision in this manner. The only known use of deep supervision is Ref. [23]; that, however, is restricted to lung nodule classification.

Another issue relates to the fact that detection, classification, and categorization are closely intertwined, and significant prior knowledge of average or atlas shapes for anatomical structures is available. Because there are no occlusions, the prior anatomical knowledge can be used directly to facilitate localization and segmentation, without the complexities arising from scaling and occlusions. A conditional random field (CRF) regularization model, in conjunction with anatomic atlases and back-tracing of the locations (voxels) responsible for the highest-scoring label (see Refs. [7-8]), can be used to this end. A typical CNN framework has early layers that focus on high-resolution responses and late layers that compute outputs with coarse representations. This strategy leads to ambiguities in pixel-level and sub-pixel level labeling which leads to challenges in prognosis from radiology where small structures are more abundant than in natural images. Bringing small structures to the attention of radiologists is vital as these elements are more likely to be missed. No existing application of deep learning to medical imaging, apart the present disclosure, can provide localization or segmentation of the lesion responsible for the class returned by the deep network.

3DCNN

It is possible to apply 3DCNN on medical image volumes in an end-to-end fashion, such that large volumetric segments or entire image volumes can be used as input data for abnormality/anomaly detection and classification. These methods include voxel level prediction of annotations such as location, size, shape and anatomical labels. The method consists in the application of convolutional filters in three spatial dimensions, as opposed to the two spatial dimensions that are currently taught in standard CNNs. The challenge is in doing so in a computationally efficient manner, and in the application to the medical imaging domain. The preferred embodiments described in the present disclosure take advantage of recent progress in computational hardware (GPUs) and software (filter banks) to implement and train a fully 3D convolutional network (see Ref [3]), but applied to the 3D imaging volume, as opposed to 2D space-and-time.

As known to the person of ordinary skill in the art, a convolutional network comprises multiple layers. Some of the layers are termed convolutional layers. An exemplary two dimensional convolution can be calculated as:

$$Y(x,y,n) = X(x,y,m) * w_n(x,y,m) = \Sigma_i \Sigma_j \Sigma_m X(x-i, y-j, m) \cdot w_n(x,y,m) \quad \text{eq. 1}$$

where Y is the output of a convolutional layer with N filters, X represents the output of the previous layer, x,y denote spatial coordinates, m denotes the $m^{th}$ channel in the input, n denotes the output channel from the $n^{th}$ filter. It can be noted that $w_n$ operates on all channels (m) at each spatial location to generate a new output with the same spatial dimensions as F, but only one output channel. Each layer can comprise several filters, producing several outputs, all of which are passed to subsequent layers as input. The outputs can be stacked together as channels and fed to the next layer.

An exemplary three dimensional convolution can be calculated as:

$$Y(x,y,z,n) = X(x,y,z,m) * w_n(x,y,z,m) = \Sigma_i \Sigma_j \Sigma_k \Sigma_m X(x-i, y-j, z-k, m) \cdot w_n(x,y,z,m) \quad \text{eq. 2}$$

where Y is the output of a convolutional layer with N filters, X represents the output of the previous layer, x,y,z denote spatial coordinates, m denotes the $m^{th}$ channel in the input, n denotes the output-channel from the $n^{th}$ filter. It can be noted that $w_n$ operates on all channels (m) at each spatial location to generate a new output with the same spatial dimensions as F, but only one output channel. Each layer can comprise several filters, producing several outputs, all of which are passed to subsequent layers as input.

Deep Supervision

In some embodiments, deep supervision can be used by applying the same supervision at multiple stages of a network. In some embodiments, the methods of the present disclosure can apply the approach of Ref. [29] to medical images by using a different domain-specific deep supervision that differs from the classification goal. In other embodiments, since many factors influence clinical decision-making, it is possible to exploit these annotations (such as location, size, shape and anatomical atlases) by incorporating them through deep supervision that differs from the main classification/detection task. For example, certain abnormalities only exist in certain anatomies. Adding a deeply supervised output to localize this anatomy early in the network can help the detection of abnormalities in that region, e.g. using deep supervision to localize the liver aids in the detection of a liver disease. This can also be applied to age or gender related classifications, using deep supervision for key factors (such as those exhibited by young or old patients) can aid in the detection of abnormalities specific to those demographics.

Fine-Scale Localization and Segmentation

The methods of the present disclosure can apply a fine scale localization technique, similar to that described in Refs. [2, 34], which incorporates lower resolution features with higher resolution features to generate new higher resolution responses with the influence of multiple scales and coarse level guidance. The network architecture of the present disclosure utilizes typical (fine-to-coarse) network responses but adds additional structure such that coarse representations are directly incorporated with higher resolution features, generating new multi-scale features that benefit from large projective fields and abstract features (typical of a generic architecture), as well as fine-scale features. This embodiment incorporates both fine (narrow context, high resolution) and coarse (large context, low resolution) responses into a single representation, allowing fine scale detections, high-resolution pixels/voxels classification (segmentation) and image/volume classification of very small structures.

The methods of the present disclosure can apply the methods of Refs. [7, 8, 11], to medical imaging, allowing identification of which voxels in the input data have the strongest influence on the classification outcome of the neural network. The methods described in the present disclosure allow exploiting the same computations used to train the network (namely back-propagation) to instead find which voxels would have the largest impact on the class labels if modified. In more details, it is possible to compute the sensitivity of the class label to changes in value at each voxel (the partial derivative of the class label with respect to changes of value at each voxel), so that voxels that have very small sensitivity do not affect the class label. Highlighting voxels with high sensitivity value is a proxy to identify which data locations triggered a particular diagnosis by the network, and therefore may contain evidence for a disease.

In some embodiments, the images and the taxonomy of a set of medical images are copied in a database and physically stored in a medium, such as a computer. Reports, images and labels associated with the images can be stored in the database. For example, labels may be "normal" (no abnormalities), "clear" (no clinically significant abnormalities), or 'abnormal' (significant abnormalities). The abnormal class may be further categorized, for example in type and severity. These labels may be image/volume wide or include a detailed location of the pathology i.e. in which image, and which pixels/voxels in that image, including possibly a bounding box or even a curve outlining where the pathology is located physically in the body. Labels may also include a wide variety of fine-grained categories indicating the region/anatomy that is normal/abnormal, as well as different medical conditions associated with that abnormality. When necessary, fine-grained labels may also be combined on-the-fly into categories of similar pathologies, e.g. many different types of bleeds may be combined into a 'bleed' label for training purposes. This process does not destroy the underlying labels. In some embodiments, labels may be attached as metadata to the image files.

Pre-Processing

Traditionally, different images are often generated from the same raw data to highlight different tissues, for instance bone or soft tissue. In pre-processing, labels generated during training for one study can be propagated to different images corresponding to the same raw data. Similarly, labels provided for one imaging section (e.g. axial) can be propagated to different sections (e.g. sagittal, coronal), which creates additional labels in images that share physical location using a single annotation. The propagation of labels, during post-processing, can save computational resources as the neural networks do not need to generate again the same labels. This feature can be useful during training as well as during testing of the network.

In some embodiments, the raw data can be processed by a technician to provide labels that are easily interpreted by humans (e.g. bone kernel, soft tissue kernel). In other embodiments, the raw data can be processed directly by the system. For example, the 3D imaging volume, as opposed to axial, coronal, and sagittal sections, can be considered in a fully automated processing method.

The data can then be filtered using metadata to determine which images are axial, coronal, sagittal, and which images are corrupted or present significant artifacts. Images that contain artifacts or are corrupted are eliminated from the training set. If spurious images are detected, such as documents requested by the physician (e.g. dosage and other reports) or other non-relevant material, these images are filtered out and eliminated from the training set.

Individual images can be determined to be axial by inspecting the metadata of all images in its parent series. In some embodiments, two methods can be used for this purpose. The first method conducts a simple search of the metadata tags for the term 'xial'. For example, the tags (0020, 4000) and (0008, 0008) can be searched. The second method inspects the image spatial direction indicated by the metadata tag associated with the direction. For example, the tag (0020, 0037) can be inspected. If the spatial direction of any image within a series is within a specified value of the ideal axial direction (in relation to the patient position) the entire series (scan) can be considered axial.

As known to the person of ordinary skill in the art, DICOM is the standard format for medical imaging data. DICOM stands for Digital Imaging and Communications in Medicine standard, a standard format for medical imaging data and meta-data. In some embodiments, DICOM validation for the given images can be determined using two methods. The first method verifies that the four character code 'DICM' is present at position 128 in each DICOM file as required by the DICOM specification. In addition, the imaging data is inspected, and specific unresolvable errors may occur while reading the DICOM image using standard libraries. These errors can be: buffer read failure, undetermined image format, and a general load image error. If any of these errors are detected, the image data is considered corrupt.

Training

In some embodiments, a computer algorithm that implements one or more machine learning algorithms, for example as described above, can be used to process the training set. For example, as discussed above, the algorithm may comprise as a component a Deep Neural Network, and specifically a Convolutional Neural Network.

The neural network is designed to classify images into classes. During the training phase, images can be presented to the network together with the class label, and the network parameters are adapted so as to minimize a cost function. Upon completion of the training phase, at test time, an image is presented to the system. The system can apply the parameters learned during training, to produce an estimate of the class label for the new image. CNNs are designed to factor out nuisance variability, for instance due to illumination. As discussed above, in medical imaging, and especially, for example, CT, the intensity value of a pixel is informative and therefore it can be advantageous to modify the architecture to account for this feature. In some embodiments, the neural network can take advantage of the informative pixel intensity as discussed in the following. This may be obtained by excluding from the architecture the normalization operators that, in typical CNNs, are used to remove intensity information from the imaging data.

CNN architectures comprise a stacked set of processing modules including convolutions, rectification, nonlinearity, normalization, etc. In some embodiments, a CNN architecture that can advantageously analyze medical images comprises a first layer tasked with learning a single bias (offset) per pixel across the entire image (e.g. an image comprising 512×512 pixels). In typical CNNs, this "bias" is a fixed mean image applied during preprocessing. By contrast, in the present disclosure the CNN can learn this bias, thereby improving its performance compared to a typical CNN. In some cases, the images are scalar-valued (e.g. CT), in other cases the images are vector-valued (e.g. MR, proton density, diffusion coefficient, T1, T2, magnetic heterogeneity, etc.). In some embodiments, a CNN architecture, according to the present disclosure, can comprise a sequence of different types of layers, such as convolutions, rectified linear units (ReLU), and max pooling layers, followed by fully connected layers akin to GoogLeNet [Ref. 33]. As known to the person of ordinary skill in the art, GoogLeNet is a type of CNN comprising a plurality of different layers of nodes.

Convolutional layers in CNNs are typically the core building blocks of a CNN. The convolution layer's parameters consist of a set of learnable filters that can be trained to detect certain features in an image. Another type of layer in CNNs is pooling, which combines spatial neighborhoods using a non-linear operator and can optionally include down-sampling. Max pooling is a type of non-linear pooling, therefore the max pooling layers can be substituted by other types of non-linear pooling layers. In some embodiments, max pooling partitions the input image into a set of non-overlapping sub-regions and outputs the maximum of each sub-region. In some embodiments, pooling layers can be located in between convolutional layers or convolutions.

Another type of layer comprises ReLUs, which can apply a non-saturating activation function. In neural networks, the activation function of a node defines the output of that node given an input or set of inputs. For ReLUs, an exemplary activation function is f(x)=max(0,x).

In some embodiments, a fully connected layer can be placed after several convolutional and max pooling layers. Neurons, or nodes, in a fully connected layer can have full connections to all activations in the previous layer. Another type of layer in CNNs is a loss layer, which specifies how the network training penalizes a deviation between the predicted and true labels. In some embodiments, the loss layer can be placed as a last, or close-to-last, layer in the CNN.

The architecture described above for an exemplary CNN represents the class of functions that are used to minimize the expected loss or other cost function, with respect to the free parameters, (such as the weights of the convolutional layers). In some embodiments, multinomial logistic loss is the cost function being minimized. However, the cost function can also be modified as described in the following.

In some embodiments, hinge loss can be applied, for mutually exclusive classes. Typically, the hinge loss refers to the threshold for a max(0,−) function. In some embodiments, multi-label tasks scores (where multiple classes may be present simultaneously) can be normalized with a probability simplex using a sigmoid function, followed by multi-label cross entropy loss. In other embodiments, scores are normalized using a soft-max function, followed by multinomial logistic loss. In some embodiments, combinations of these functions and loss functions are used, for example certain classes may be mutually exclusive and a soft-max function may be advantageous, whereas others may be independent and a sigmoid function may be suitable.

In some embodiments, the dataset can be divided into network training sets, network validation sets and clinical validation sets. All of these sets contain mutually exclusive studies, i.e. no part of a study may appear in two or more sets. For example, network training and validation sets are composed of images, or volumes (three-dimensional images), which are used to train and validate networks to correctly score inputs. The clinical validation set contains only study level labels, and it can be used to validate report generation only (see later for report description).

Figure 2:
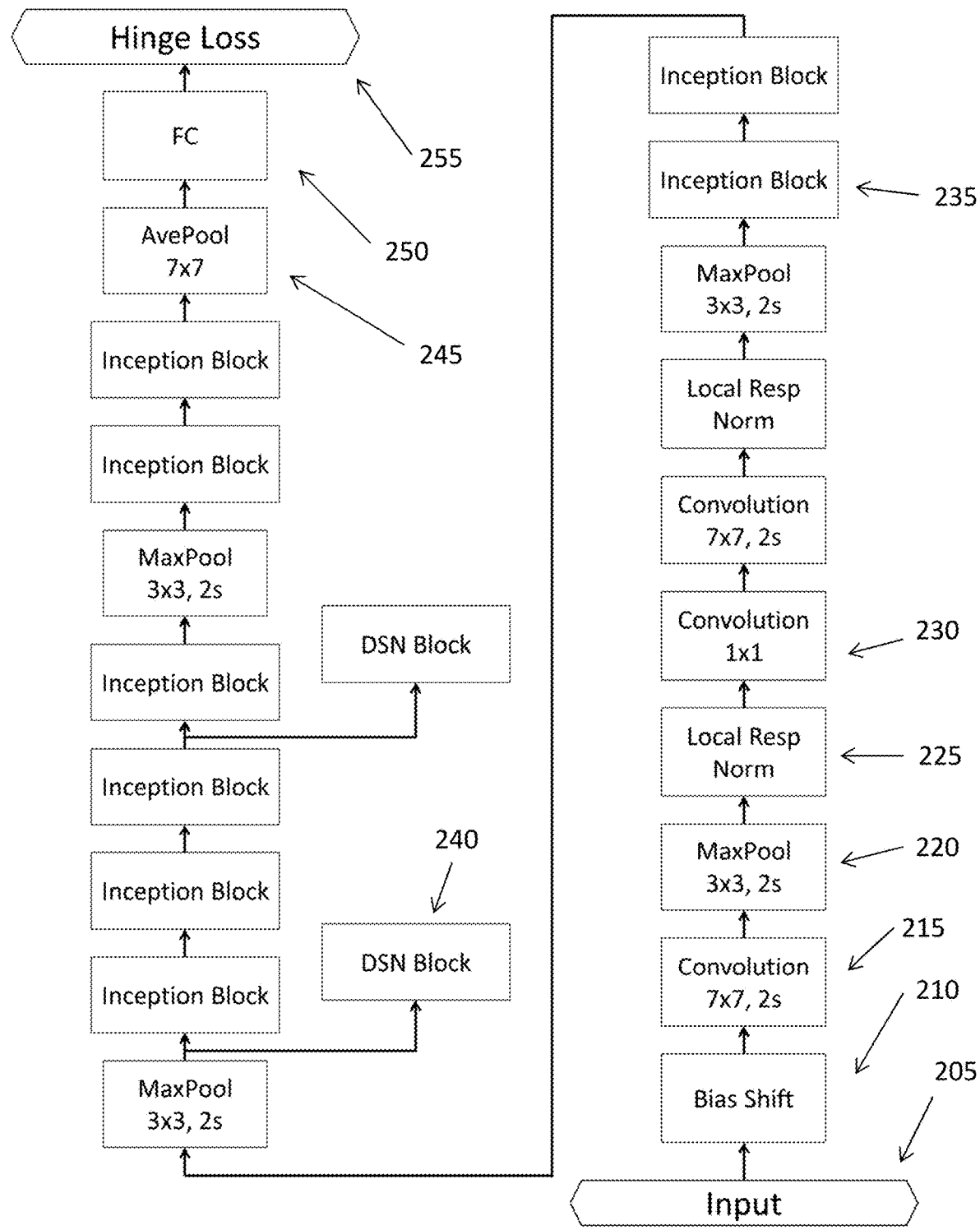
FIG. 2 illustrates an exemplary network architecture comprising several layers.

FIG. 2 illustrates an exemplary network architecture comprising several layers. In other embodiments, a different network comprising different layers may be used to detect and categorize medical anomalies. In the example of FIG. 2, the network starts with an input (205), for example 2D or 3D medical imaging data, followed by a bias layer (210). As described above in the present disclosure, CNNs normally include a fixed bias. However, the present disclosure, in some embodiments, describes how the bias can be learnt, instead, thereby improving the network performance applied to medical images.

The bias layer (210) is followed, in FIG. 2, by a convolutional layer (215). For example, a 7×7 convolutional layer (215) may be used. As known to the person of ordinary skill in the art, a layer has dimensions, for example a height and width for a 2D layer, expressed in pixels or neurons. A 7×7 layer will generally comprise 49 parameters. However, different layers having different dimensions and number of parameters may be used. In this example, layer (215) has a stride value of 2 ("2s"). As known to the person of ordinary skill in the art, the stride is the pixel shift across an image for each application of that specific layer's function. For example, a convolution for a convolutional layer, or a max pooling filter for a max pooling layer. In this example, layer (215) shifts by two pixels.

Figure 4:
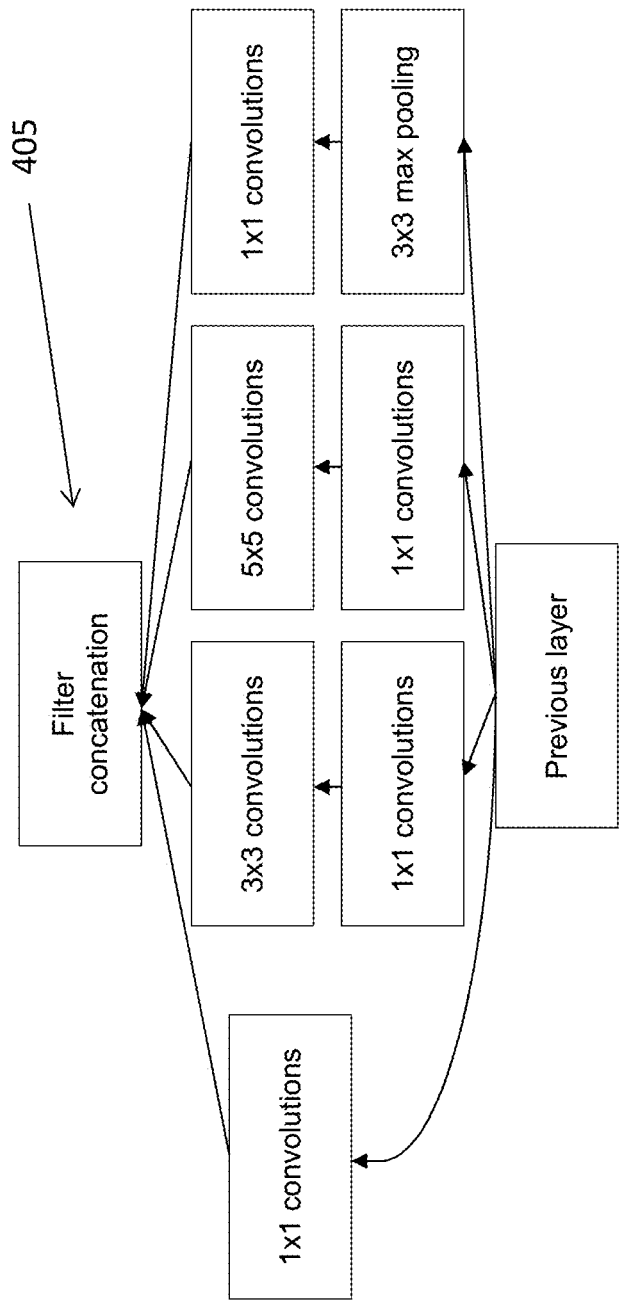
FIG. 4 illustrates an exemplary inception block.

Subsequent layers in FIG. 2 comprise a max pooling layer (220), with dimensions 3×3 and also a stride of 2. Other layers can comprise a local response layer (225), additional convolutional layers (230) and other building blocks of a network. For example, the inception block (235) represents multiple layers as described, for example, in FIG. 4. FIG. 4 comprises four different layer pathways, each having its own set of filters, the different layers converging into a filter concatenation (405) which stacks the outputs together. The exemplary inception block of FIG. 4 is discussed in Ref. 32. Other types of blocks may be used, as understood by the person of ordinary skill in the art.

The local response normalization layer (225) of FIG. 2 can perform "lateral inhibition" by normalizing over local input regions. For example, in the local response layer, each input value can be divided by $$(1+(\alpha/n)\Sigma_i x_i^2)^\beta \qquad \text{eq. 3}$$

where n is the size of each local region, $\alpha$ and $\beta$ are fixed parameters, $x_i$ is an input pixel, and the sum is taken over the region centered at that value.

In FIG. 2, the network comprises multiple inception blocks, as well as additional pooling layers, an average pooling layer (245), a fully connected layer (250), followed by hinge loss (255). The average pooling layer is similar to the max pooling layer, but uses an average instead of finding the max value. As understood by the person of ordinary skill in the art, hinge loss calculations can be used during training and testing of the network. If the training is ongoing, hinge loss can be calculated for each additional imaging data that is classified or categorized. However, if no training or testing is being carried out, the network can analyze the imaging data to return a class or category, without the hinge loss layer (255).

Figure 3:
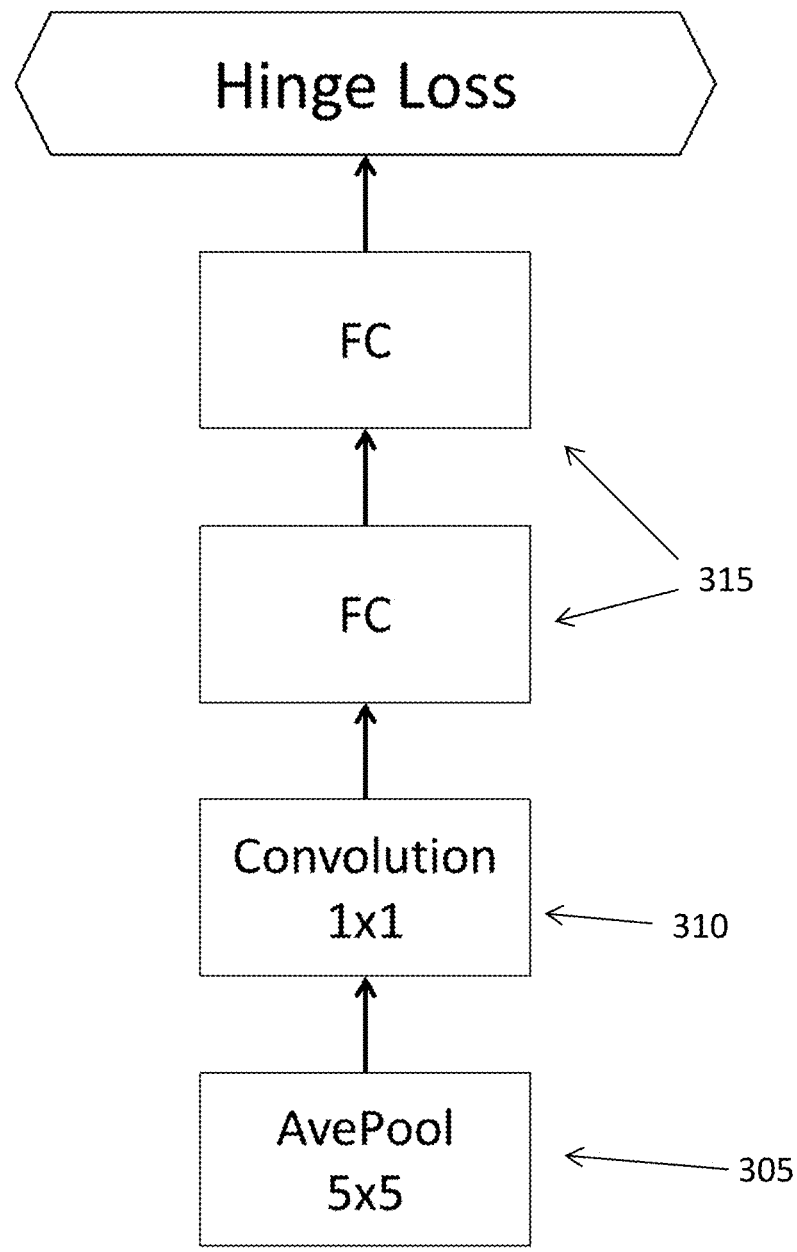
FIG. 3 illustrates an exemplary DSN block.

In embodiments using deep supervision, additional hinge loss layers can be used at intermediate depth of the network, for example in the deeply-supervised nets (DSN) block (240). DSN blocks carry out deep supervision to enhance training of the network. Hinge loss calculations determine whether the output of the network corresponds to the ground truth of the data. For example, if the imaging data contains a medical anomaly, the network should return a classification of the medical anomaly. If the output does not return the correct classification or categorization, the hinge loss calculation can back-propagate to adjust the network parameters in such a way as to return the proper classification for the medical data. Therefore, the hinge loss functions are used to adjust the network parameters, to optimize its performance and accuracy. The network can also be run with fixed parameters, after training, without back-propagation, that is with forward propagation only. In deep supervision, one or more DSN blocks can calculate hinge loss at intermediate depths. FIG. 3 illustrates an exemplary DSN block, comprising, for example, an average pooling layer (305), a convolutional layer (310), and two fully connected layers (315).

Data Augmentation

In some embodiments, in order to train the networks of the present disclosure to handle additional variation in data, it is possible to augment the data before training. Augmentation amounts to perturbing the available training data by applying to it nuisance transformations. In this manner, the network learns to be robust against such factors. For example, three types of simple augmentation can be applied to the data comprise scale, rotation and mirroring.

During training, each image may be modified by any combination of the following operations: 1) the image may be rotated by a specific angle, for example +/−25 degrees; 2) the image may be rescaled by a specific percentage, for example +/−10% of its original size; 3) the image may be mirrored. In some embodiments, the use of the specific values of +/−25 degrees and +/−10% is advantageous in augmenting the data, compared to other possible values for the rotation angle and the scaling factor. The values above were found to optimally simulate various patient positions and reduce position nuisance during training.

In some embodiments, 3D augmentation methods can be applied for both 3D and 2D training operations. If an abnormality in an image is localized (e.g. the center voxel is given), additional augmentation can be generated by out-of-plane rotation about a given physiologically acceptable point. This simulates patient movement, once coupled with translational insensitivity of the network architecture. This method can be used for 3D convolution training, while new 2D images can be generated through standard interpolation along a given axis (axial, coronal and sagittal). For example, it may be useful to apply a rotation about a point in 3D that would simulate the movement of the patient. For example, for imaging data referring to the head it may be advantageous to rotate an image about the base of the skull, in amounts similar to typical head movements.

Other augmentation methods may be used as necessary, through simulation of various artifacts, including ring artifacts, Poisson and Gaussian noise, beam hardening, beam scattering, edge effects, and out of field, reconstruction errors.

Balancing

Ordinarily, in deep learning based image classification, a roughly equal number of images for each class is presented. In some embodiments, since there is a preponderance of normal imaging data in medical images, the "clear" class can be deflated so as to achieve a balance of approximately 20%/80% rather than the actual average incidence. Since occurrence of many abnormalities in medical images is rare, and the physical space occupied by these pathologies may be small, e.g. one-two slices out of 100 in a study, there can be extreme class imbalances.

For example, given two classes, 'A' and 'B', in a given study, for a class to be considered 'A' all images must belong to the 'A' class, whereas class 'B' is inherited by the study when any image belongs to 'B'. For a given exemplary population, 10% of studies are class B and 60% are class A. For class 'B' studies, approximately 10% of images indicate 'B'. If a dataset contains 100 studies and all studies have 100 images, in a scenario where all images with known classes are used, the above percentages would lead to 6000 individual images in class A, and 100 images of class 'B'. This creates a ratio of 60:1 between class A and B.

Reducing the class imbalance in scenarios such as these can be handled through deflation of class A. In some embodiments, three methods for deflation can be applied to overrepresented classes: 1) restrict the number of over-represented labeled studies in each dataset, 2) reduce data augmentation on over-represented labeled images and 3) restrict the amount of data collected from each study from the over-represented class. For example, given the above scenario, only 50% of class 'A' studies and 10% of images in those studies would be trained on, at a time. As a consequence, a more manageable class balance of 5:1 between A and B can be achieved. In other embodiments, other methods to reduce class imbalances may be applied.

Ensembles

In some embodiments, an ensemble of networks may be trained, instead of a single network. These networks can be trained with the same data, and each network may perform slightly differently from the other networks. In some embodiments, the data may be modified to a greater or smaller degree, for each network. For example, small modifications of the data may comprise a reordering of the data, where the order refers to the sequence with which they are processed during training. An overall classifier can be obtained by averaging the results of each classifier in the ensemble of networks.

Balancing is a factor in how ensembles are built as well. In general, ensembles can be built by training the same or similar networks on the same data in a different order than other members of the ensemble. The ensemble generates a set of scores from each member in the ensemble, and scores can be aggregated together. The aggregation leads to a boost in performance, and decreases the effect of classifier noise.

In the ensembles of the present disclosure, an additional component relating to class balancing can be used when generating ensembles. Starting with an initial ensemble, new networks can be trained on data that generates inaccurate or uncertain scores from the current ensemble. This process can boost performance on difficult samples, without adding data that the system already processes accurately, while maintaining class balance as described above.

In addition, for the 3D and single 2D images, some network classifiers can use multiple spatially correlated slices as input for a single classification. Typically, CNNs use channels that represent different color spaces, e.g. RGB channels. Many classifications in natural images require color information to make a determination, however radiological images may require spatial context instead. This context could be added by selecting a number of neighboring images along the acquisition plane, or by using multiple images that share a point in 3D.

One possible method to capture spatial context comprises feeding small batches of adjacent images ("channels") to the image being processed. Similarly to the color processing of an RGB image, which comprises three images (one image per color channel, red, green and blue), it is possible to train a network with small batches of images. For examples, groups of three or more images may be used for each batch. A convolutional network normally performs two-dimensional convolutions, in the sense that filters are translated in two dimensions; however, the filters directed at capturing spatial context can span in three dimensions: two spatial dimensions and the third dimension comprising the "channels". A channel corresponds to a filter that performs a convolution on the layer's input. Given an image, convolution with each filter produces an output that has the same spatial dimensionality of the image (in two dimensions, x, y). A layer is composed of a collection of filters, and each filter provides one response map so that the complete output of the layer is comprised of each output for each filter leading to a layer output with an additional dimensions for each filter output, i.e. x,y,m, where x, y are the spatial dimensions of the input and m corresponds to the number of channels in the image. These channels are akin to RGB channels in natural images, where each channel represents different representations of the same image. In a RGB representation, each channel corresponds to the three chromaticities of the red, green, and blue.

Another possible method to capture spatial context comprises performing true 3D convolutions. This method is a generalization of the method above, where batches of images (possibly the entire volume of the study) are fed to the network but the filters translate in all three spatial dimensions. In other words, all three dimensions are treated equally. This implementation is more computationally intensive, both to train and to test.

As indicated above, ensembles of networks can produce more accurate scores than those produced by either one of the individual networks constituting the ensemble. However, producing scores for each network incurs additional computational costs. A single network can be trained to output the same scores as an ensemble through a process called 'knowledge distillation' [Ref 33]. In this process, the network is trained to not only classify inputs, but also to produce scores that match those produced by an ensemble.

Application

In some embodiments, after the system is trained, the weights of the network are fixed, and the network is embodied as an algorithm running on a computer or server that receives as input new, previously unseen data (test set, or test datum), and produces an output.

In some embodiments, a study can be received and stored in memory. Metadata can also be stored. Whenever an image is received, the image is either added to a study or a new study is created. Once a new study is created, it can be queued for classification by the network. In some embodiments, the classification has a timer and can be blocked until there are no changes to the study for a given interval (e.g., 30 seconds). If the study is below a certain number of images, possibly indicative of a transmission or storage error, it can be rejected and not processed. Accepted studies are processed by the CNN, a series (scan/volume) at a time. The network computation may be distributed onto different computers. The classification can return raw scores for every image in a study. These scores can be saved on disk, in memory, or in a database.

In some embodiments, classification scores can be used in two ways: 1) a score is compared to a threshold, and if above the threshold, it is flagged for a particular classification, or 2) the maximum score across all scores may be used to flag each image. Depending on the type of classification, all images in the study may inherit that classification if one, some, or all images in a study are flagged with a particular classification. For example, if any image is flagged with a particular pathology, that flag may be inherited by the entire study. In contrast, only when all images in the study are flagged as 'normal' would the 'normal' flag be inherited by the study. In other words, if the pathology is visible in only one image of the study pertaining to a patient, the entire study can be classified as abnormal even though a subset of the images does not show the pathology.

In some embodiments, an algorithm can analyze the study-wide flags and produce an overall classification for the study as normal or abnormal. The algorithm can also categorize the nature of the abnormality in the report. Flags and categories can be derived from the taxonomy created by physicians in the taxonomy for the dataset. These taxonomies can be grouped into broad categories that relate to a particular physiology, and which are commonly used by human radiologists. These broad categories generally include, for example, 'BRAIN', 'SINUS', 'ORBIT', and 'BONES'. Flags from these categories may overlap with each other. These flags can be used to determine the details to be included in the reports, and the overall categorization of the report as normal or abnormal.

The output of the network can be transmitted to the report system that can use simple logic to generate a human readable report. For example, a simple lookup table can be used, which selects pre-formatted text based on the flags and categories assigned to that study and inserted into the report. Specific details are inserted into preformatted text where required, e.g. which image contains a particular abnormality or quantitative descriptions such as mass size in millimeters.

Post-Processing

The medical inference integration layer software integrates the inbound DICOM image header metadata with the output of the neural networks applied to the images. This system produces a clinically appropriate output reflecting both the actual imaging data and the overall clinical situation of the patient. While there are many different possible embodiments for this post-processing stage, in general the concept relates to introducing a processing stage between the deep network and the decision stage, whether by a trained medical professional or the final patient. This stage can be designed and engineered exploiting user studies, human-computer interface studies, domain-specific knowledge, and natural language processing. In some cases, this post-processing stage includes visualization methods to enable the user to see through the volume, including but not limited to Virtual Reality (VR) displays, or navigation methods to traverse through the volume that is conformal to what is currently practiced by physicians and radiologists.

System Embodiments

The image data may be transferred from the medical imaging facility via VPN or SSL in a HIPAA compliant fashion to a central facility for processing by the integration medical inference engine and the deep learning networks. The clinically relevant interpretation of the data can be returned to the appropriate healthcare providers via the same secure method once the analysis is complete. Additional training and improvements of the system can be accomplished via periodic upgrades to the local software.

Alternatively, the integration medical inference and deep learning software may be installed locally on the medical imaging device or EMR system at the medical imaging facility and the analysis performed at the local facility. Additional training and improvements of the local system can be accomplished via periodic upgrades to the local software.

The output of the system may be communicated to an Emergency Department for assisted triage and to help expedite the treatment of the patient. Information may also be provided to the physicians signing off the report indicating specific images and location of pathology to assist the physicians to improve the report interpretation accuracy.

The system can generate revenue through fees charged for usage of the system by hospitals, clinics, physicians, patients, Medicare and insurance providers.

In yet another embodiment, the software running the CNN as well as the post-processing stage may be operated on a client device. As portable devices become increasingly powerful, and include dedicated processing units such as GPUs or DSP, processing could be performed locally at the end-user device (patient or medical professional). The entire system may run on mobile devices or be integrated into the imaging system for the convenience of the patient and local healthcare facilities. Additional training and improvements of the local system can be accomplished via periodic upgrades to the local software.

The system may be used on a social network allowing its members to upload medical images for a second opinion on their medical imaging study. In yet another embodiment, the software could be run though a social network, where patients can upload or link to the site of their data, and through the communication and computation infrastructure of a social network, such as those operate by Facebook™, Yahoo™, Amazon™, Google™, Microsoft™, or any other Cloud Computing service, the patients can receive a report or diagnosis or interpretation. In other words, the software in conjunction with cloud computing could provide a "second opinion" on data previously collected at a medical facility.

The training data can be collected from patient information from hospitals and clinics and always preserves all privacy laws including HIPPA.

The system can use feedback from physicians on the accuracy of its reports. The information is always transmitted in a secure fashion observing all privacy laws including HIPPA. This information can be used to further train the system for improved accuracy and performance.

When reviewing a report produced by the system for signature, the physician can make any changes prior to signing the report. These changes are captured and used to further improve the system by retraining.

The system can be designed to allow "lifelong learning" whereby errors detected by the system or by human professionals at any stage of the processing pipeline, all the way to errors that eventually result in patient harm or malpractice suit, can be fed back to the system and become part of the training set. In a particular embodiment, particularly challenging cases can be treated as "hard samples" and can be mined for training.

Regulatory Issues

In some embodiments, the present disclosure is implemented through a processor and memory configured to: receive imaging data relating to a body part of a human patient, for example a brain scan according to different medical techniques; classify the imaging data into a normal or an abnormal class; for the abnormal class, spatially localize an abnormality within the imaging data of the body part, for example the location of a tumor in the brain; and categorize the abnormality within a medical category, for example by categorizing the abnormality as a tumor, or a certain type of tumor. In some embodiments, the categorization can be carried out with standard medical categories, or it may also be carried out using non-standard categories. For example, categories can be created to categorize the abnormalities, with each category having specific information associated with it, such as the type or severity of the abnormality. In some embodiments, rotating an image is carried out by a rotation angle up to +/−50 degrees, and a scaling factor between +/−5% and +/−40%. The rotation angle may also be referred to as zero to 50 degrees, considering that the positive rotation can be redefined. The scaling factor can also be referred to as 5 to 40%, considering that the factor may be a reducing or magnifying factor.

Figure 6:
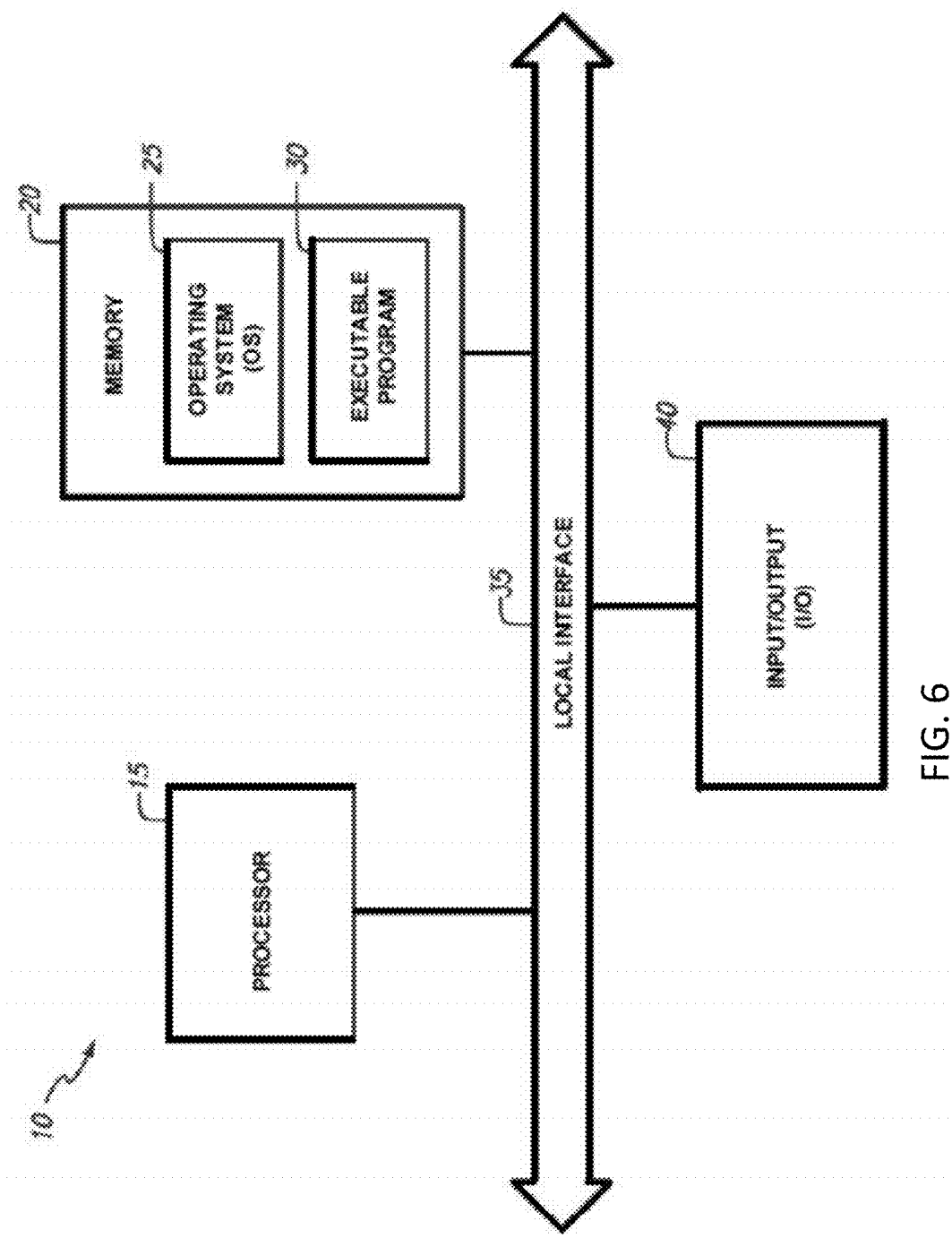
FIG. 6 depicts an exemplary embodiment of target hardware for implementation of an embodiment of the present disclosure.

FIG. 6 is an exemplary embodiment of a target hardware (10) (e.g., a computer system) for implementing the embodiments of FIGS. 1-5. This target hardware comprises a processor (15), a memory bank (20), a local interface bus (35) and one or more Input/Output devices (40). The processor may execute one or more instructions related to the implementation of FIGS. 1-5, and as provided by the Operating System (25) based on some executable program (30) stored in the memory (20). These instructions are carried to the processor (15) via the local interface (35) and as dictated by some data interface protocol specific to the local interface and the processor (15). It should be noted that the local interface (35) is a symbolic representation of several elements such as controllers, buffers (caches), drivers, repeaters and receivers that are generally directed at providing address, control, and/or data connections between multiple elements of a processor based system. In some embodiments the processor (15) may be fitted with some local memory (cache) where it can store some of the instructions to be performed for some added execution speed. Execution of the instructions by the processor may require usage of some input/output device (40), such as inputting data from a file stored on a hard disk, inputting commands from a keyboard, inputting data and/or commands from a touchscreen, outputting data to a display, or outputting data to a USB flash drive. In some embodiments, the operating system (25) facilitates these tasks by being the central element to gathering the various data and instructions required for the execution of the program and provide these to the microprocessor. In some embodiments the operating system may not exist, and all the tasks are under direct control of the processor (15), although the basic architecture of the target hardware device (10) will remain the same as depicted in FIGS. 1-5. In some embodiments a plurality of processors may be used in a parallel configuration for added execution speed. In such a case, the executable program may be specifically tailored to a parallel execution. Also, in some embodiments the processor (15) may execute part of the implementation of FIGS. 1-5, and some other part may be implemented using dedicated hardware/firmware placed at an Input/Output location accessible by the target hardware (10) via local interface (35). The target hardware (10) may include a plurality of executable programs (30), wherein each may run independently or in combination with one another.

The methods and systems described in the present disclosure may be implemented in hardware, software, firmware or any combination thereof. Features described as blocks, modules or components may be implemented together (e.g., in a logic device such as an integrated logic device) or separately (e.g., as separate connected logic devices). The software portion of the methods of the present disclosure may comprise a computer-readable medium which comprises instructions that, when executed, perform, at least in part, the described methods. The computer-readable medium may comprise, for example, a random access memory (RAM) and/or a read-only memory (ROM). The instructions may be executed by a processor (e.g., a digital signal processor (DSP), an application specific integrated circuit (ASIC), a field programmable logic array (FPGA), a graphic processing unit (GPU) or a general purpose CPU.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] Lee et al., C.-Y. Lee, S. Xie, P. Gallagher, Z. Zhang, and Z. Tu. Deeply-supervised nets. *AISTATS*, 2015.

[2] Honari et al., S. Honari, J. Yosinski, P. Vincent, and C. Pal, "Recombinator Networks: Learning Coarse-to-Fine Feature Aggregation," arXiv.org, vol. cs.CV. 23 Nov. 2015.

[3] Tran et al., Du Tran, L. Bourdev, R. Fergus, L. Torresani, and M. Paluri, "Deep End2End Voxel2Voxel Prediction," arXiv.org, vol. cs.CV. 20 Nov. 2015.

[4] M. Lai. Deep Learning for Medical Image Segmentation. arXiv.org, vol. cs.LG. 8 May 2015.

[5] Wang et al., 2015: L. Wang, C.-Y. Lee, Z. Tu, S. Lazebnik. Training Deeper Convolutional Networks with Deep Supervision. ArXiv 1505.02496, May 11, 2015.

[6] Merkow et al. "Structural Edge Detection for Cardiovascular Modeling." *Medical Image Computing and Computer-Assisted Intervention—MICCAI* 2015. Springer, 2015. 735-742.

[7] A Mahendran, A Vedaldi—Understanding deep image representations by inverting them, arXiv preprint arXiv:1412.0035, 2014

[8] K Lenc, A Vedaldi—Understanding image representations by measuring their equivariance and equivalence, arXiv preprint arXiv:1411.5908, 2014

[9] K. P. Murphy. Machine Learning, a Probabilistic Perspective. MIT Press, 2012.

[10] A Krizhevsky, I Sutskever, G E Hinton, Imagenet classification with deep convolutional neural networks, Advances in neural information processing systems, 1097-1105, 2012

[11] A Kirillov, D Schlesinger, W Forkel, A Zelenin, S Zheng, P Torr, C Rother, A Generic CNN-CRF Model for Semantic Segmentation, arXiv preprint arXiv:1511.05067, 2015

[12] D. E. Rumelhart, G. E. Hinton, R. J. Williams. Learning representations by back-propagating errors. Nature 323, p. 533-536, 1986.

[13] Saver J L, Fonarow G C, Smith E E, Reeves M J, Grau-Sepulveda M V, Pan W, Olson D M, Hernandez A F, Peterson E D, Schwamm L H. Time to treatment with intravenous tissue plasminogen activator and outcome from acute ischemic stroke. JAMA. 2013 June; 309(23): 2480-8

[14] Bershad E M, Rao C P, Vuong K D, Mazabob J, Brown G, Styron S L, Nguyen T,

[15] Delledera E, Smirnakis S M, Lazaridis C, Georgiadis A L, Mokracek M, Seipel T J,

[16] Nisbet J J, Baskaran V, Chang A H, Stewart P, Suarez J I. Multidisciplinary protocol for rapid head computed tomography turnaround time in acute stroke patients. J Stroke Cerebrovasc Dis. 2015 June; 24(6): 1256-61

[17] Gunn A J, Mangano M D, Pugmire B S, Sahani D V, Binder W D, et al. Toward Improved Radiology Reporting Practices in the Emergency Department: A Survey of Emergency Department Physicians. J Radiol Radiat Ther 2013 1(2): 1013

[18] Alexander J. Towbin, Srikant B. Iyer, James Brown, Kartik Varadarajan, Laurie A. Perry, David B. Larson. Practice Policy and Quality Initiatives: Decreasing Variability in Turnaround Time for Radiographic Studies from the Emergency Department. RadioGraphics, March 2013, Vol. 33: 361-371, 10.1148/rg.332125738

[19] Wong W Sl, Roubal I, Jackson D B, Paik W N, Wong V K, Outsourced teleradiology imaging services: an analysis of discordant interpretation in 124,870 cases, J Am Coll Radiol. 2005 June; 2(6):478-84.

[20] Brady A, Laoide R Ó, McCarthy P, McDermott R. Discrepancy and Error in Radiology: Concepts, Causes and Consequences. The Ulster Medical Journal. 2012; 81(1):3-9

[21] Pinto A, Brunese L. Spectrum of diagnostic errors in radiology. World Journal of Radiology. 2010; 2(10):377-383. doi:10.4329/wjr.v2.i10.377

[22] Engl, Heinz Werner, Martin Hanke, and Andreas Neubauer. Regularization of inverse problems. Vol. 375. Springer Science & Business Media, 1996.

[23] W. Shen, M. Zhou, F. Yang, C. Yang, and J. Tian, "Multi-scale Convolutional Neural Networks for Lung Nodule Classification," in IPMI, 2015

[24] Rumelhart et al., Learning internal representations by error propagation, Parallel distributed processing: explorations in the microstructure of cognition, vol. 1, pages 318-362, MIT Press Cambridge, Mass., USA, 1986

[25] Du Tran, L. Bourdev, R. Fergus, L. Torresani, and M. Paluri, "Deep End2End Voxel2Voxel Prediction," arXiv.org, vol. cs.CV. 20 Nov. 2015.

[26] H. R. Roth, L. Lu, A. Farag, H. C. Shin, and J. Liu, "DeepOrgan: Multi-level Deep Convolutional Networks for Automated Pancreas Segmentation," arXiv.org. 2015.

[27] W. Shen, M. Zhou, F. Yang, C. Yang, and J. Tian, "Multi-scale Convolutional Neural Networks for Lung Nodule Classification," IPMI, 2015.

[28] Y. Zheng, D. Liu, B. Georgescu, H. Nguyen, and D. Comaniciu, "3D Deep Learning for Efficient and Robust Landmark Detection in Volumetric Data"

[29] K. Lee, A. Zlateski, V. Ashwin, and H. S. Seung, "Recursive Training of 2D-3D Convolutional Networks for Neuronal Boundary Prediction," Advances in Neural Information Processing Systems, 2015, pp. 3559-3567.

[30] K. He, X. Zhang, S. Ren, and J. Sun, "Deep Residual Learning for Image Recognition," arXiv.org, vol. cs.CV. 10 Dec. 2015.

[31] Engl, Heinz Werner, Martin Hanke, and Andreas Neubauer. Regularization of inverse problems. Vol. 375. Springer Science & Business Media, 1996

[32] Szegedy, Christian, et al. "Going deeper with convolutions." Proceedings of the IEEE Conference on Computer Vision and Pattern Recognition. 2015.

[33] Hinton, Geoffrey, Oriol Vinyals, and Jeff Dean. "Distilling the knowledge in a neural network." arXiv preprint arXiv:1503.02531, 2015.

[34] Merkow, Jameson, David Kriegman, Alison Marsden, and Zhuowen Tu. "Dense Volume-to-Volume Vascular Boundary Detection. "International Conference on Medical Image Computing and Computer-Assisted Intervention. Springer International Publishing, 2016.

[35] M. Sun, T. X. Han, M.-C. Liu, and A. Khodayari-Rostamabad, "Multiple Instance Learning Convolu-tional Neural Networks for Object Recognition," arXiv.org, October 2016.

[36] R. Girshick, J. Donahue, T. Darrell, and J. Malik, "Rich feature hierarchies for accurate object detection and semantic segmentation," in *Computer Vision and Pattern Recognition*, 2014.

[37] R. Girshick, "Fast r-cnn," in *International Conference on Computer Vision (ICCV)*, 2015.

[38] S. Ren, K. He, R. Girshick, and J. Sun, "Faster R-CNN: Towards real-time object detection with region proposal networks," in *Advances in Neural Information Processing Systems (NIPS)*, 2015.

What is claimed is:

1. A medical device for analysis of medical imaging data to diagnose abnormalities and generation of corresponding reports via a taxonomy of labels, the medical device comprising:
   a processor and memory configured to implement the steps of:
   implementing computer code of a convolutional neural network (CNN), the CNN comprising a plurality of layers in a sequence, each layer comprising a plurality of nodes;
   receiving imaging data relating to a body part of a human patient, taken at a medical imaging facility;
   receiving the taxonomy of labels describing a plurality of normal and abnormal conditions for the body part, the taxonomy of labels describing the normal and abnormal conditions in the imaging data;
   classifying by the CNN the imaging data into a normal or an abnormal class by selecting or not selecting each label of the taxonomy of labels;
   for the abnormal class, spatially localizing by the CNN an abnormality within the imaging data of the body part;
   categorizing by the CNN the abnormality within a category; and
   generating a first report based on selected and not selected labels of the taxonomy of labels;
   wherein:
   the first report is compared to a second report prepared by a human expert;
   if the first report does not match the second report, a corresponding label discrepancy is sent to another human expert to review the label discrepancy, and the CNN is retrained based on the label discrepancy,
   each node of each layer is connected to at least one other node of a subsequent or preceding layer in the sequence,
   each node accepts an input value and outputs an output value,
   the plurality of layers comprises convolutional layers, rectified linear unit layers, non-linear pooling layers and fully connected layers,
   training of the CNN comprises feeding the CNN with previous imaging data and corresponding previously generated reports by the medical device corrected by a human expert to include correction of the selected and not selected labels of the taxonomy of labels, and
   the medical imaging data comprises at least one of X-ray slides, computerized tomography, magnetic-resonance (MR), diffusion-tensor (DT), functional MR, gene-expression data, dermatological images, and optical imaging of tissue slices.

2. The medical device of claim 1, wherein the CNN is trained by deep supervision based on known anatomy of the body part.

3. The medical device of claim 1, wherein the processor and memory are further configured to compare the first report with a second report prepared by a human expert.

4. A computer-implemented method for analysis of medical imaging data and generation of corresponding reports via a taxonomy of labels, the method comprising:
   implementing in a computer a convolutional neural network (CNN), the CNN comprising a plurality of layers in a sequence, each layer comprising a plurality of nodes, wherein:
   each node of each layer is connected to at least one other node of a subsequent or preceding layer in the sequence,
   each node accepts an input value and outputs an output value, the nodes in the CNN comprise parameters;
   receiving, by the computer, imaging data relating to a body part of a human patient,
   receiving, by the computer, the taxonomy of labels describing a plurality of normal and abnormal conditions for the body part, the taxonomy of labels describing the normal and abnormal conditions in the imaging data;
   classifying by the CNN the imaging data into a normal or an abnormal class by selecting or not selecting each label of the taxonomy of labels;
   for the abnormal class, spatially localizing by the CNN an abnormality within the imaging data of the body part;
   categorizing by the CNN the abnormality within a category;
   preparing a first report based on the selected and not selected labels;
   comparing the first report with a second report prepared by a human expert; and
   if the first report does not match the second report, sending a corresponding label discrepancy to the human expert, and requesting the human expert to review the label discrepancy,
   wherein:
   the plurality of layers comprises convolutional layers, rectified linear unit layers, non-linear down-sampling layers and fully connected layers,
   training of the CNN comprises feeding the CNN with previous imaging data and corresponding previously generated reports by the medical device corrected by a human expert to include correction of the selected and not selected labels of the taxonomy of labels, and
   the medical imaging data comprises at least one of X-ray slides, computerized tomography, magnetic-resonance (MR), diffusion-tensor (DT), functional MR, gene-expression data, dermatological images, and optical imaging of tissue slices.

5. The method of claim 4, further comprising, following the human expert resolving the label discrepancy in favor of the second report, requesting further review by a second human expert on the label discrepancy.

6. The method of claim 5, further comprising, following the second human expert resolving the label discrepancy in favor of the second report, retraining the CNN based on the label discrepancy.

7. The method of claim 5, further comprising, following the second human expert resolving the label discrepancy in favor of the first report, providing feedback on the label discrepancy to the first human expert.

\* \* \* \* \*

UNITED STATES PATENT AND TRADEMARK OFFICE
CERTIFICATE OF CORRECTION

PATENT NO.         : 10,692,602 B1
APPLICATION NO.    : 15/707918
DATED              : June 23, 2020
INVENTOR(S)        : Kim Nguyen et al.

Page 1 of 1

It is certified that error appears in the above-identified patent and that said Letters Patent is hereby corrected as shown below:

On the Title Page

Item (73), entitled "Assignee," currently reads:
"(73) Assignee: DEEPTRADIOLOGY, INC., Santa Monica, CA (US)"

Please replace this text with:
"(73) Assignee: DEEPRADIOLOGY, INC., Santa Monica, CA (US)"

Signed and Sealed this
First Day of September, 2020

Andrei Iancu
*Director of the United States Patent and Trademark Office*